US010377085B2

United States Patent
Lupinetti et al.

(10) Patent No.: US 10,377,085 B2
(45) Date of Patent: Aug. 13, 2019

(54) DEVICE AND METHOD FOR FORMING ULTRASONIC WELDS ON WEB MATERIALS IN CONTINUOUS MOVEMENT

(71) Applicant: Fameccanica.Data S.p.A., Pescara (IT)

(72) Inventors: Serafino Lupinetti, Elice (IT);
Francesco D'Aponte, Pescara (IT);
Alessandro D'Andrea, Pescara (IT);
Domenico Polidori, Pescara (IT)

(73) Assignee: FAMECCANICA.DATA S.p.A, Pescara (IT)

( * ) Notice: Subject to any disclaimer, the term of this patent is extended or adjusted under 35 U.S.C. 154(b) by 415 days.

(21) Appl. No.: 15/154,054

(22) Filed: May 13, 2016

(65) Prior Publication Data
US 2016/0332361 A1 Nov. 17, 2016

(30) Foreign Application Priority Data

May 15, 2015 (IT) .................. 102015000015284

(51) Int. Cl.
*B32B 37/00* (2006.01)
*B29C 65/08* (2006.01)
(Continued)

(52) U.S. Cl.
CPC ........ *B29C 65/08* (2013.01); *A61F 13/15585* (2013.01); *A61F 13/15699* (2013.01);
(Continued)

(58) Field of Classification Search
CPC ... B29C 65/08; B29C 65/086; B29C 66/0326; B29C 66/1122; B29C 66/232;
(Continued)

(56) References Cited

U.S. PATENT DOCUMENTS 3,562,041 A 2/1971 Robertson
4,504,539 A * 3/1985 Petracek ............... B29C 65/086
156/296

(Continued)

FOREIGN PATENT DOCUMENTS

EP 0582286 A1 2/1994
EP 0702622 A1 3/1996
(Continued)

OTHER PUBLICATIONS

Machine translation of Japanese Office Action dated May 15, 2018, issued in Japanese Patent Application No. 2016-096245.
(Continued)

*Primary Examiner* — James D Sells
(74) *Attorney, Agent, or Firm* — Patterson + Sheridan, LLP

(57) ABSTRACT

Apparatus for forming transversal welds on a composite web material, comprising at least two superimposed sheets of material, suitable for use in the production of sanitary articles, comprising: a feeding unit including first and second feeding means configured to advance the composite web along a main straight direction X at a speed $V_1$. an ultrasonic welding unit 80 arranged between the first and second feeding means, comprising at least one ultrasound source coupled to a sonotrode having a flat welding surface and an anvil unit having at least one anvil element movable along a closed path, which has a straight portion parallel to the main direction X.

12 Claims, 12 Drawing Sheets

(51) Int. Cl.
*A61F 13/15* (2006.01)
*B29C 65/00* (2006.01)
*B29L 31/48* (2006.01)

(52) U.S. Cl.
CPC .. *A61F 13/15731* (2013.01); *A61F 13/15739* (2013.01); *A61F 13/15756* (2013.01); *A61F 13/15764* (2013.01); *B29C 65/086* (2013.01); *B29C 66/0326* (2013.01); *B29C 66/1122* (2013.01); *B29C 66/232* (2013.01); *B29C 66/431* (2013.01); *B29C 66/8167* (2013.01); *B29C 66/81427* (2013.01); *B29C 66/81435* (2013.01); *B29C 66/81465* (2013.01); *B29C 66/8242* (2013.01); *B29C 66/83521* (2013.01); *B29C 66/9221* (2013.01); *B29C 66/92431* (2013.01); *B29C 66/92653* (2013.01); *B29C 66/961* (2013.01); *A61F 2013/15869* (2013.01); *B29C 66/433* (2013.01); *B29C 66/93431* (2013.01); *B29C 66/944* (2013.01); *B29C 66/949* (2013.01); *B29L 2031/4878* (2013.01)

(58) Field of Classification Search
CPC ............ B29C 66/431; B29C 66/81427; B29C 66/81435; B29C 66/81465; B29C 66/8167; B29C 66/8242; B29C 66/83521; B29C 66/9221; B29C 66/92431; B29C 66/92653; B29C 66/961
USPC ....................................................... 156/580.1
See application file for complete search history.

(56) References Cited

U.S. PATENT DOCUMENTS

| | | |
|---|---|---|
| 6,676,054 B2 | 1/2004 | Heaney et al. |
| 7,383,865 B2 | 6/2008 | Umebayashi et al. |
| 2010/0116409 A1 | 5/2010 | Yamamoto |
| 2013/0167629 A1 | 7/2013 | Ninomiya et al. |

FOREIGN PATENT DOCUMENTS

| | | |
|---|---|---|
| EP | 0920977 A1 | 6/1999 |
| EP | 1013585 A1 | 6/2000 |
| EP | 2460644 A1 | 6/2012 |
| EP | 2460645 A1 | 6/2012 |
| GB | 2257652 A | 1/1993 |
| JP | 2002254522 A | 9/2002 |
| JP | 2013216023 A | 10/2013 |
| JP | 2014524265 A | 9/2014 |
| WO | 2013027390 A1 | 2/2013 |

OTHER PUBLICATIONS

Italian Search Report and Written Opinion dated Feb. 9, 2016 for Application No. 102015000015284.

* cited by examiner

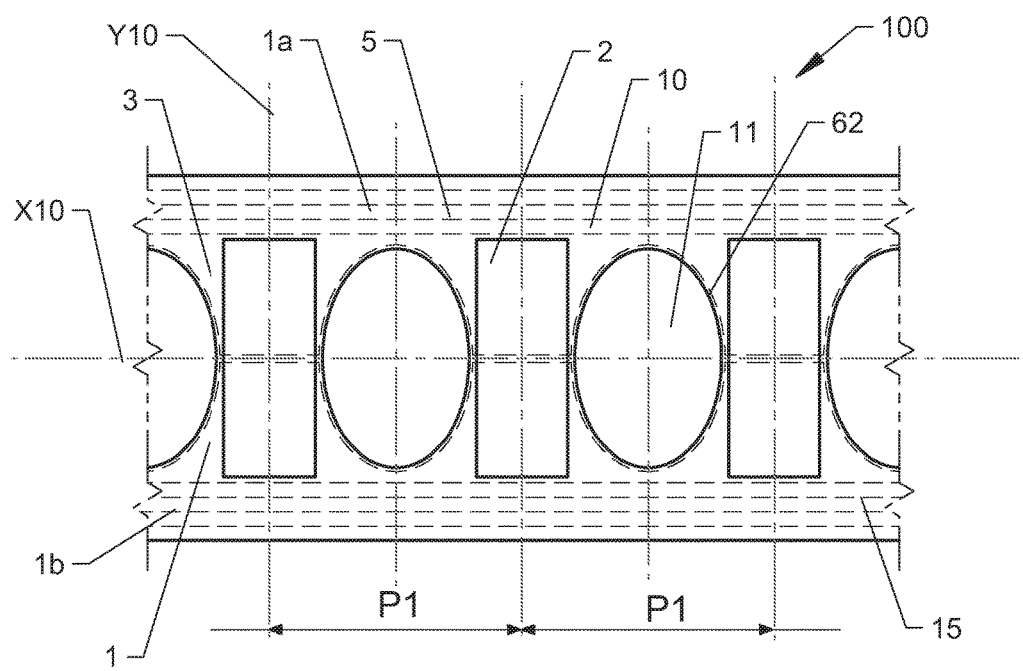
FIG: 3a
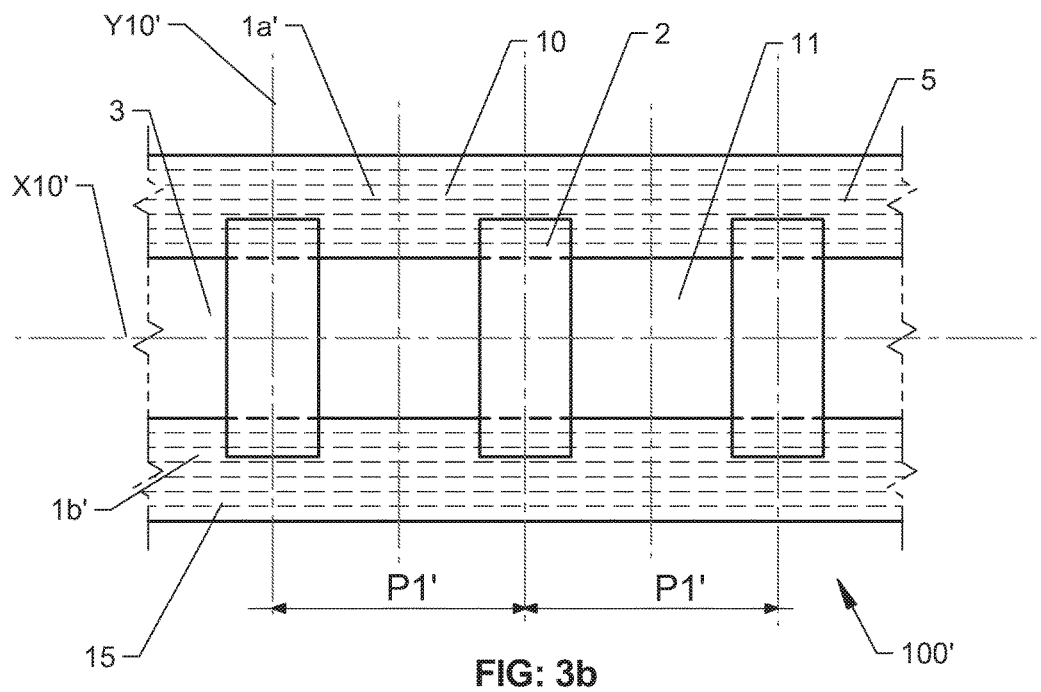
FIG: 3b

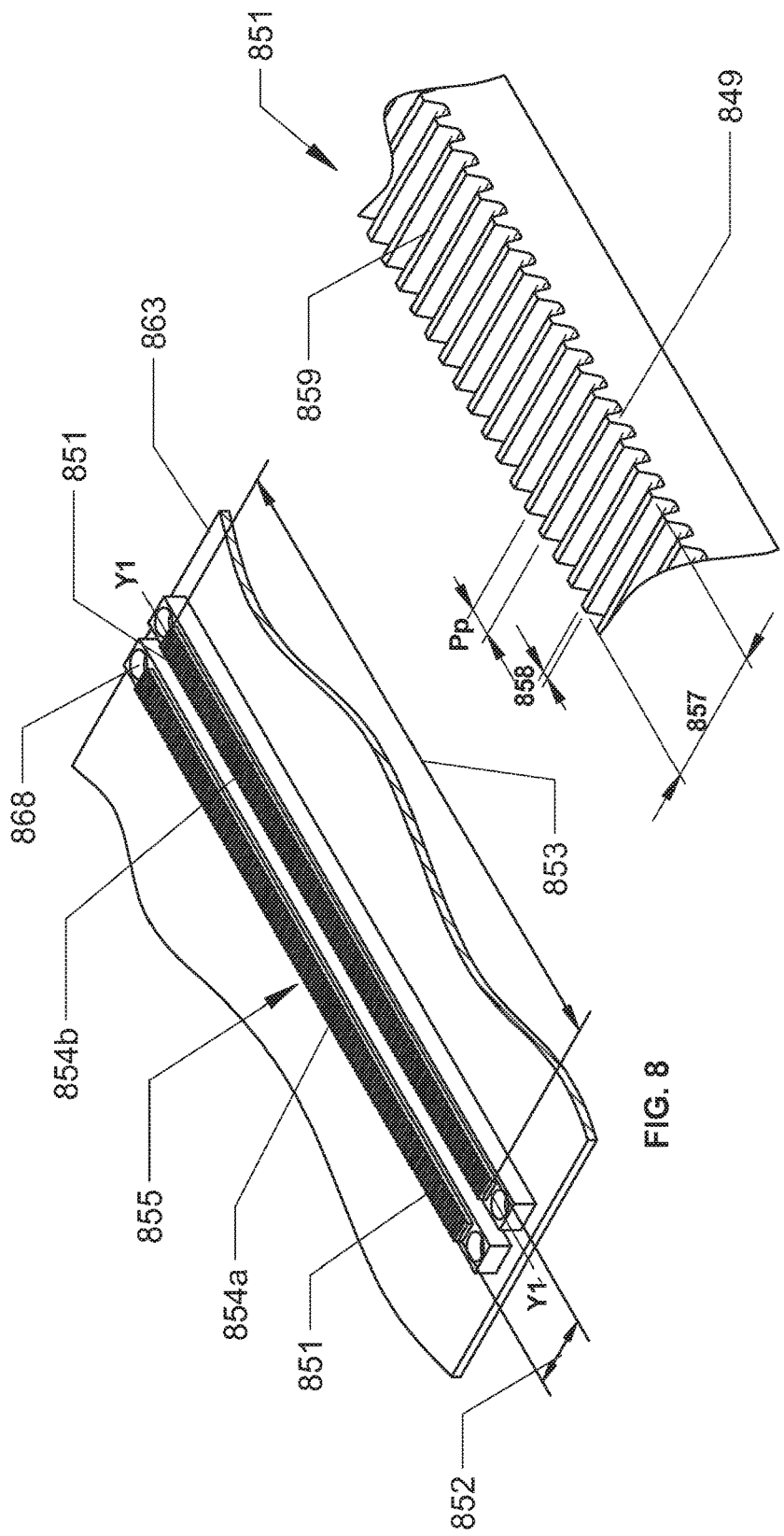

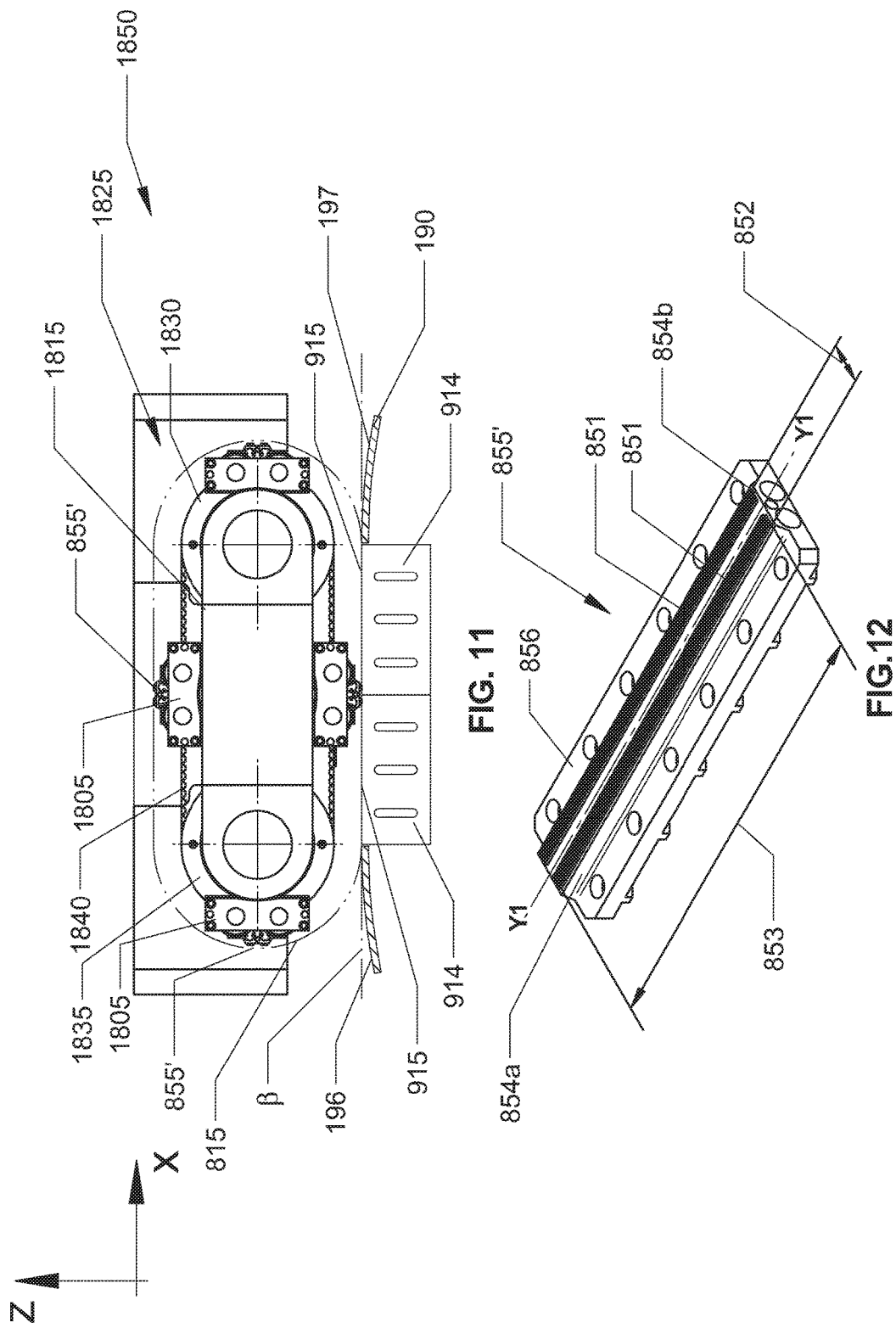

DEVICE AND METHOD FOR FORMING ULTRASONIC WELDS ON WEB MATERIALS IN CONTINUOUS MOVEMENT

CROSS-REFERENCE TO RELATED APPLICATIONS

This application claims benefit of Italian patent application number 102015000015284, filed May 15, 2015, which is herein incorporated by reference.

BACKGROUND OF THE INVENTION

Field of the Invention

The present description relates to ultrasonic welding apparatuses for welding web materials that move continuously along a main direction.

The present description has been developed with particular attention to the sector of sanitary products. The description is, however, capable of being applied to many other sectors such as, for example, the automatic packaging industry.

Description of Prior Art

Ultrasonic welding has been employed for some time in various sectors of the art, in practice for use in all situations in which applying ultrasonic vibrational energy is possible to obtain the localized fusion of the materials.

The ultrasonic devices for carrying out the welding of two or more strips of superimposed material apply a forging-type process. That is, the welding is implemented by repeatedly striking the layers of material interposed between a vibrating device of the ultrasound system (or sonotrode) and the protuberances of a corresponding contrast (or anvil) element.

Due to the repeated blows inflicted by the vibrating element against the anvil element, the material interposed between them heats up and melts locally, exactly at the protuberances of the contrast element.

Over the years, an increasing interest has developed in the possibility of carrying out ultrasonic welding operations in dynamic production processes, typically on a web material that advances at a fairly high speed.

It is obvious that to obtain an acceptable weld in these cases it is necessary to provide a minimal amount of ultrasonic energy which, however, can vary greatly depending on the type of materials which have to be welded, the number of sheets of which they are composed and the shape and the number of protuberances of the anvil element.

In fact, relative to the latter point, it is known that technologies for forming continuous lines of ultrasonic welds, which extend parallelly to the advancing direction of the web material are consolidated and give excellent results.

However, this is not true when it comes to forming welds that extend transversely to the advancing direction of the material and that are spaced apart from each other, known as intermittent welds.

In the latter case, the ultrasonic welding technology encounters a series of difficulties due to the fact that the intermittent welds highlight the sensitivity of ultrasonic systems with respect to some characteristic parameters of the welding process. One of these parameters is that regarding the relative position (or gap) of the sonotrode relative to the outer surface of the anvil element, between which the web material subjected to welding advances.

Another extremely important factor is the permanence time of the material between the components of the welding device, during which the vibrating element or sonotrode provides the ultrasonic energy required to produce a quality weld. However, it is evident that the aforesaid permanence time decreases with increasing feeding speeds of the material.

To attempt to eliminate, or at least reduce, the aforesaid criticalities, much energy has been expended, as demonstrated by numerous documents such as, for example, EP-A-0 702 622, U.S. Pat. No. 7,383,865, EP-A-0 920 977, in which solutions are described which maintain the gap between the sonotrode and the anvil element constant during the welding operations, or which increase the permanence time of the web material in the ultrasonic device during the welding step, by instantaneously varying the advancing speed of the web material.

The technical solutions found, although having given positive results from a qualitative point of view of the welds, have ample room for improvement and numerous drawbacks linked, in particular, to the complexity of the mechanical devices and the control of the proposed solutions, both regarding the relative position (or gap) of the sonotrode relative to the anvil element and regarding the instantaneous variation devices of the speed of the web material to increase the permanence time.

These latter devices, among other things, can also present the drawback of inducing unwanted tension variations in the web material to be welded, which result in an uncontrolled variability of the length of the finished product.

SUMMARY OF THE INVENTION

The object of the present invention is that of providing an apparatus and the relative method for the transverse welding of a composite web by means of the application of vibrational energy (ultrasonic) that overcomes the previously highlighted limitations present in currently known systems.

The apparatus of the present invention is, therefore, particularly suitable for forming transverse intermittent welding lines on a composite web material comprising at least two superimposed sheets capable of being used, for example, for producing closed-type sanitary articles wearable as pants, including the case in which it is used in production lines operating at high production speeds.

According to the present invention, this object is achieved thanks to an apparatus and to the relative method of implementation, whose characteristics are referred to specifically in the claims that follow.

The attached claims form an integral part of the disclosure provided here in relation to the invention.

BRIEF DESCRIPTION OF THE DRAWINGS

The invention will now be described, purely by way of non-limiting example, with reference to the attached figures, in which:

FIGS. 3a and 3b represent the composite webs formed of semi-finished blanks of two types of absorbent products of the pre-closed pant-type producible with the apparatus according to an embodiment of the present invention.

FIG. 8 is a schematic perspective view of an anvil element of the anvil unit of FIG. 5b.

FIG. 9 is a schematic perspective view of a detail of the anvil element of FIG. 8.

FIG. 11 is a schematic side view of the anvil unit of FIG. 10.

FIG. 12 is a schematic perspective view of an anvil element of the anvil unit of FIG. 11.

DETAILED DESCRIPTION

In the following description various specific details are illustrated aimed at a thorough understanding of the embodiments. The embodiments can be implemented without one or more of the specific details, or with other methods, components, materials, etc. In other cases, known structures, materials, or operations are not shown or described in detail to avoid obscuring various aspects of the embodiments.

The reference to "an embodiment" in the context of this description indicates that a particular configuration, structure or characteristic described in relation to the embodiment is included in at least one embodiment. Therefore, phrases such as "in an embodiment", possibly present in different places of this description do not necessarily refer to the same embodiment. Furthermore, particular conformations, structures, or characteristics can be combined in any suitable manner in one or more embodiments without, therefore, limiting the principle and/or the scope of the invention.

Figure 1:
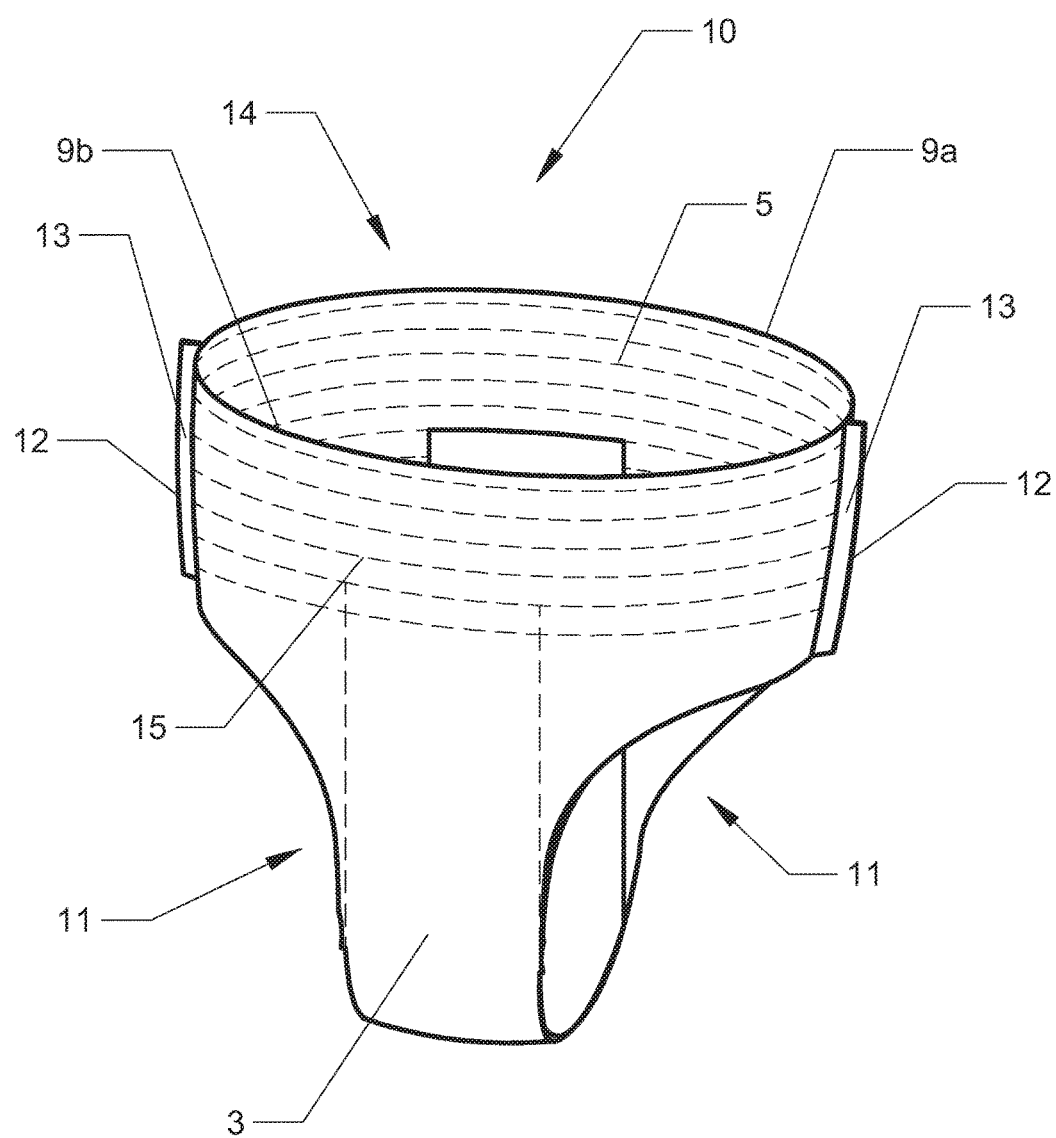
FIG. 1 is a perspective view of an absorbent product of the pre-closed pant-type producible with the apparatus according to an embodiment of the present invention, in the closed configuration ready for use.

In FIG. 1, a sanitary article 10 is represented, which can be produced with a method and an apparatus in accordance with the disclosures provided by the present invention.

In FIG. 1, the absorbent article 10 is shown in its closed condition, where it has a conformation similar to that of pants.

Figure 2A:
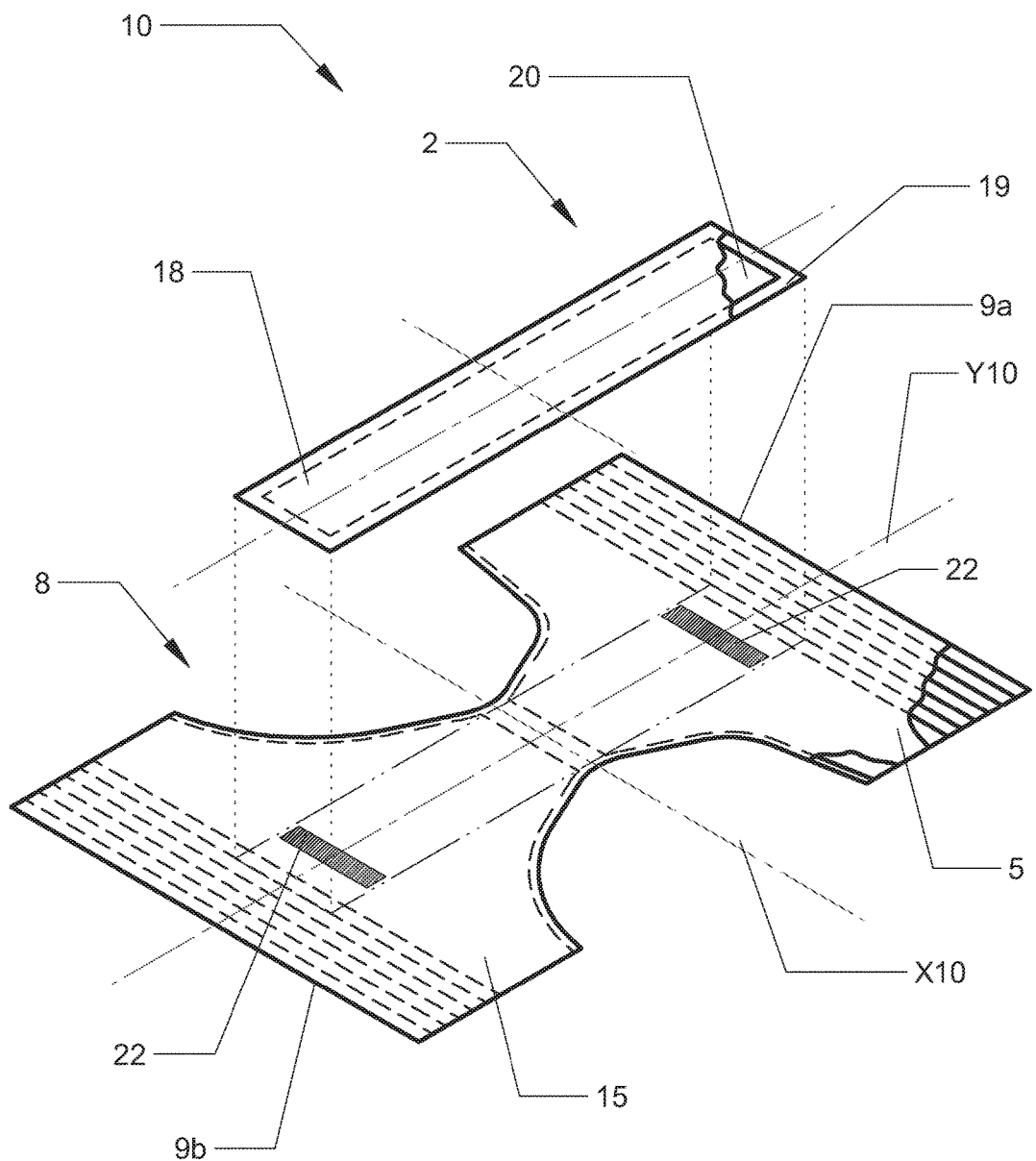
FIG. 2a is a schematic exploded perspective view of the absorbent product of FIG. 1 in the open extended configuration, highlighting the main components.
Figure 2B:
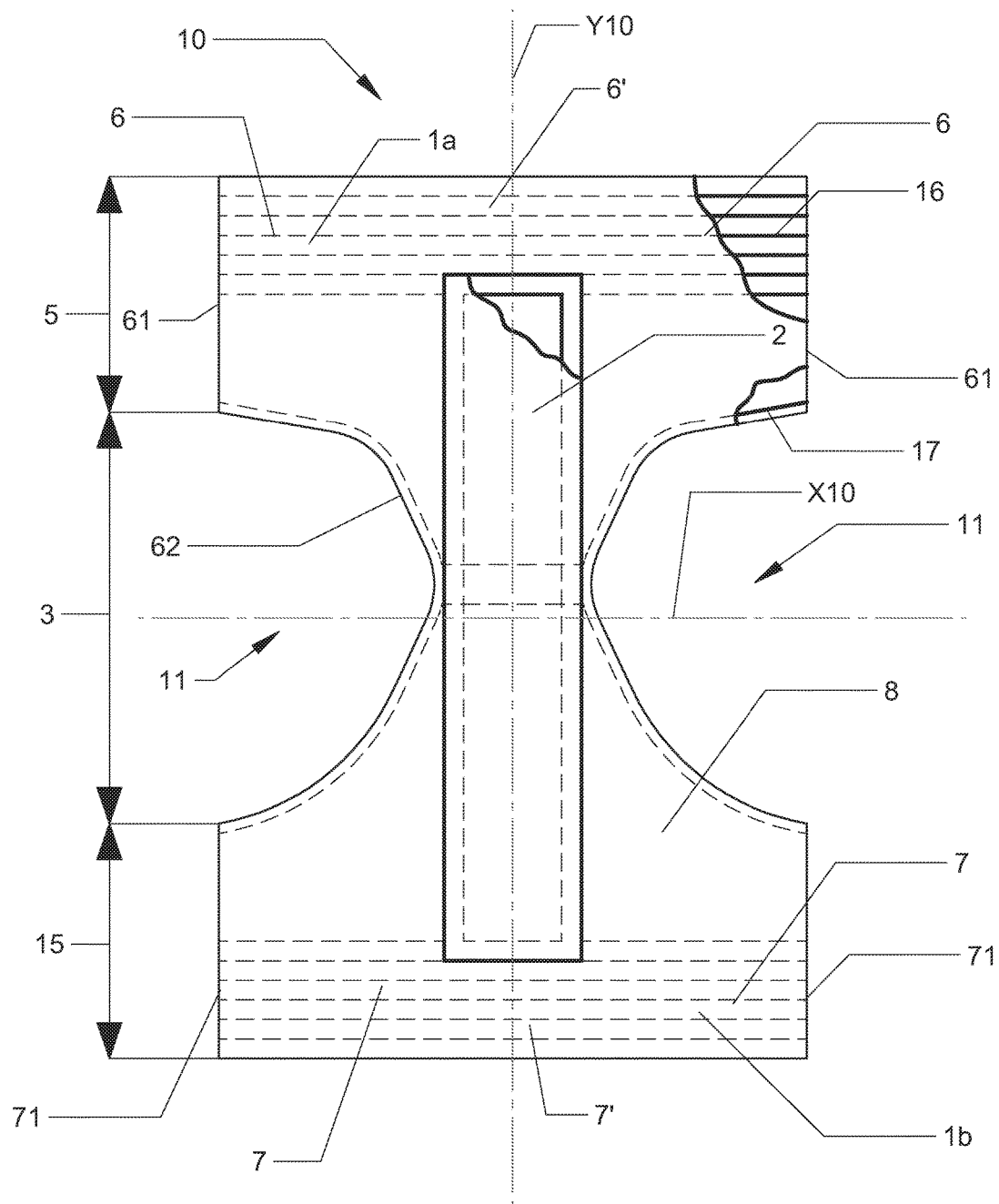
FIG. 2b is a schematic plan view of the absorbent product of FIG. 1 in the open extended configuration.

In FIGS. 2a and 2b, the same disposable absorbent sanitary article 10 of FIG. 1 is represented. In FIG. 2a, the sanitary article 10 is shown in an exploded perspective view in order to highlight the two main elements that compose it:
the support structure or chassis 8, and
the absorbent insert 2.

FIG. 2b is a schematic plan view of the absorbent article 10 in the open extended configuration.

In FIG. 2b, in the chassis 8 it is possible to identify:
A first or front waist region 5,
A second or rear waist region 15,
A crotch region 3 located between the two waist regions 5, 15,
a longitudinal axis $Y_{10}$, and
a transverse axis $X_{10}$ perpendicular and equidistant, respectively, from the side edges 61 and 71 and from the end edges 9a and 9b of the two waist regions—front 5 and rear 15.

In the first waist region 5, it is possible to identify a pair of first side panels or front panels 6 separated by a first central waist region 6' interposed between them. Similarly, in the second waist region 15, it is possible to identify a second central waist region 7', which separates the waist panels 7.

In order to assume its pant configuration, the absorbent article 10 is typically folded about its transverse axis $X_{10}$, overlapping the two waist regions 5 and 15 together, so as to be able to carry out the transversal welding 13 that join the distal edges 61 and 71 of the side panels of the absorbent article 10 and that confer the characteristic pant-formation, defining the opening of the waist 14 and the two openings for the legs 11, as shown in FIG. 1.

In general terms, we can say that in the absorbent article 10, the first and the second waist regions 5 and 15 are typically elasticated, for example, with elastic elements 16 in threads, and which are interconnected to each other by the crotch region 3 in which, typically, the absorbent insert 2 is present.

The first and the second waist regions 5 and 15 are elasticated as they are designed to maintain the absorbent insert 2 adherent to the user's body in a comfortable manner, even when it becomes heavy after having absorbed body fluids.

Absorbent articles of this type can have different configurations, both regarding the absorbent insert 2, and regarding the front 5 and rear 15 waist regions.

In FIGS. 3a and 3b, two embodiments are represented, by way of example, for producing sanitary articles 10 and 10' in which the continuous webs 100 and 100' formed of the semi-finished blanks have different structures from each other which, however, can be treated with ultrasonic devices.

In FIG. 3a, the front waist regions 5, the rear waist regions 15 and the crotch region 3 of the absorbent article 10 are produced with a single web 1 on which a series of cuts 62 are typically made, of a suitable shape, each of which contributes to define the contour of the openings of the legs 11 of two consecutive sanitary articles 10. The absorbent insert 2 is typically placed between two consecutive cuts 62.

In the absorbent article 10' that is obtained from the chain of blanks of FIG. 3b, the first and the second waist regions 5, 15 are formed by two webs 1a' and 1b', which are distinct and typically parallel to each other.

The two webs 1a' and 1b' are joined together by the absorbent insert 2 which, in this way, contributes in itself to form the crotch region 3 and the openings for the legs 11.

For both absorbent articles 10 and 10', the absorbent insert 2 has a structure that can typically comprise:
a top layer or topsheet 18 permeable to evacuated body fluids, designed to be facing towards the user's body;
a lower layer or backsheet 19 impermeable to body fluids; and
an absorbent core 20, interposed between the topsheet 18 and the backsheet 19, provided to absorb and retain exudates.

On the absorbent product 10, and in particular on the absorbent insert 2, other elements may be present, which contribute to increase the characteristics of wearability and absorbency, all well known to persons skilled in the sector and of which extensive documentation is available.

In the illustrated embodiment, the absorbent insert 2 can have a typically rectangular shape with the longer sides parallel to the longitudinal axis $Y_{10}$ of the absorbent article 10.

The absorbent insert 2 and the web 1 can be made integral with each other by means of adhesive strips 22 and/or by means of welds formed using any system known per se, such as, for example, mechanical thermo-welding or ultrasonic welding.

Figure 4:
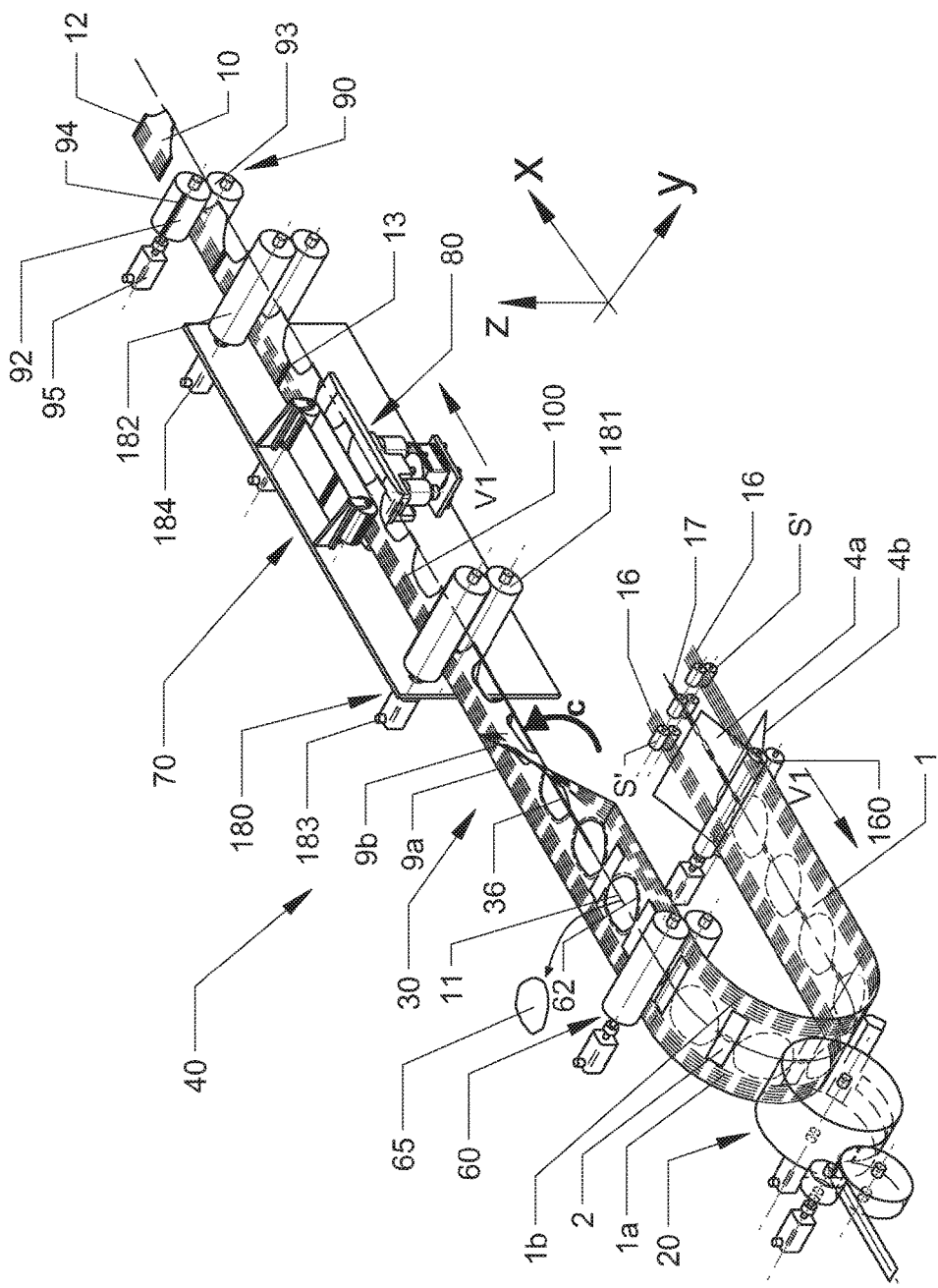
FIG. 4 is a perspective schematic view of the production steps of an absorbent article according to an embodiment of the present invention.

As already mentioned, the two types of sanitary articles 10 and 10', despite having structural differences, can both be produced by the production method 40 according to the embodiment illustrated in FIG. 4.

Below, therefore, apart from specific references, the description will be carried out of the method 40 of the embodiment illustrated in FIG. 4, with reference to the sanitary article 10 illustrated in FIGS. 1, 2 and 3a without, for this, removing the genericity from the discussion.

In the manufacturing method shown in FIG. 4, it is possible to identify a main (or longitudinal) direction X and a transverse direction Y, which define a plane β (beta) parallel to the movement plane of the web material 100 and which are parallel and orthogonal, respectively, to the direction of flow of the web material 100.

In addition, it is possible to identify a vertical direction Z orthogonal to both the longitudinal direction X and the transverse direction Y.

In the embodiment of FIG. 4, the production method 40 of the absorbent sanitary article 10 includes a first step in which the web 1 is produced by coupling together a first sheet 4a to a second sheet 4b in a fixing station 160, with the suitably stretched elastic elements 16 interposed between them.

The first sheet 4a and the second sheet 4b, in combination with the elastic elements 16, form a first elastic waist band 1a and a second elastic waist band 1b, each of which contributes to form the first waist region 5 and the second waist region 15 of the absorbent sanitary article 10, respectively.

The first sheet 4a and the second sheet 4b can be supplied to the fixing station 160 by respective web material unwinding devices, not illustrated in FIG. 4, but of a type known in the art, such as, for example, the one described in application EP 1 013 585 A1 by the same applicant.

Similarly, the elastic elements 16 can be fed to the fixing station 160 by an unwinding device S' of a known type such as, for example, the unwinder for elastic materials in a reel described in U.S. Pat. No. 6,676,054.

In the embodiment, as shown in FIG. 4, during the lamination step of the first and second sheets 4a and 4b with the elastic elements 16, it is possible to insert additional elastic elements 17 provided for elasticizing the leg openings 11 so as to confer a greater wearability to the absorbent article 10.

In the embodiment, the first and the second sheets 4a and 4b can be, preferably, made of non-woven fabric superficially treated with chemicals products, which accentuate their water-repellent characteristics, so as to contain any leaks of liquid and to avoid any possible contamination of the user's clothing with which the sanitary article 10 typically comes into contact.

The elastic elements 16 and 17, in turn, can be selected from several materials available on the market such as, for example, synthetic rubber strips produced by Fulflex, or it is possible to use Lycra® thread products from Invista.

It is evident, however, that a wide range of natural or synthetic materials is available on the market, conveniently usable for producing an absorbent sanitary article 10.

In the embodiment illustrated in FIG. 4, after having produced the web 1 the absorbent inserts 2 are joined to it, by means of the application device 20 known in the art, forming a composite web 100 composed of a continuous chain of semi-finished blanks aligned in order to have the transverse axis $X_{10}$ of each absorbent article 10 oriented parallelly to the main direction X of the production line flow.

In the embodiment illustrated in FIG. 4, at the crotch region 3, a series of cuts 62 are made, of suitable shape, by means of the shaped cutting unit 60.

Each of the cuts 62 remove a portion of material 65 from the web 1, contributing to define the contour of the openings of the legs 11 of two consecutive sanitary articles 10 which, in the preferred embodiment illustrated in FIGS. 3a and 4, can be circumscribed by the elastic threads for the legs 17.

In the manufacturing process 40 of the absorbent sanitary article 10, according to the embodiment illustrated in FIG. 4, once the composite web 100 is produced, consisting of a chain of semi-finished blanks of absorbent sanitary articles 10, the first and the second waistbands 1a and 1b can be superimposed on each other by matching the respective longitudinal edges 9a and 9b.

The superimposing operation of the two waistbands can be implemented by longitudinally bending the composite web material 100 around the bar 36 of the longitudinal folding station 30.

In the longitudinal folding station 30, the bar 36, around which the web material 100 is wound during the bending, is typically parallel to the first main direction X and coincides with the transverse axis $X_{10}$ of each of the sanitary articles 10 forming the composite web 100.

In FIG. 4, the arrow C indicates schematically the bending movement that results in obtaining the superimposition of the two waistbands 1a and 1b.

An example of suitable equipment for creating a bend of this type is described in the application TO2011A001085 by the same Applicant.

After having carried out the bending operation about the transverse axis $X_{10}$, and having superimposed the first waistband 1a and the second waistband 1b of the web 100, the bands 1a and 1b can be joined together at regular intervals by means of welds 13, as illustrated in the absorbent article of FIG. 1.

Each of the weld lines 13, in order to join together the opening edge of the waist 14 and the opening edge for the legs 11, typically extends for a length L, measured in a direction transverse to the advancing direction of the web material 100. This is together with a width T, measured in the main direction X, typically of the order of about 1 centimeter.

As a guide, without the intention of being limitative in the scope of the invention, the size L of the welding lines 13 can vary according to the type of absorbent article (if intended for children or for adults) from a minimum of 90 mm to a maximum of 240 mm.

The width T of the welding lines 13, or rather the dimension in the advancing direction X, can vary from a minimum of 5 to a maximum of 13 mm.

The welds 13 on the composite web material 100 can be produced using the welding apparatus 70.

In the embodiment, illustrated in FIG. 4, the welding apparatus 70 typically comprises an ultrasonic welding unit 80 interposed between a first feeding means 181 and a second feeding means 182 of a feeding unit 180, which cause the composite web material 100 to advance along the main straight direction at a speed $V_1$.

The first and the second feeding means 181 and 182 can be any one of the devices for feeding web materials that are known in the art such as, for example, feeding systems with a motorized belt or with rollers. In the embodiment illustrated in the attached Figures, the feeding devices 181 and 182 are two pairs of motorized rollers.

Both devices are equipped with suitable drive means 183 and 184, which are able to confer a linear advancing speed to the rollers of the two feeding devices equal to that of the web 100.

The two feeding devices 181 and 182 are also provided with mechanical means, known per se, able to clamp the continuous portion of the web 100 between them, typically coinciding with the two superimposed waistbands 1*a* and 1*b*.

Furthermore, in order to increase the capacity of gripping the web 100, one or both rollers may be of the type "under suction" or "vacuum", or rather, with a perforated outer cylindrical surface and connected to a sub-atmospheric pressure source with means known per se, so as to increase the capacity of the overall grip applicable to the continuous band of the web 100.

In the embodiment illustrated in FIG. 4, the first feeding device 181 has the purpose of feeding the web 100, composed of the chain of blanks of absorbent articles 10, to the ultrasonic welding unit 80, while the second feeding device 182 has the function of feeding the web material 100 to the successive cutting station 90. The feeding unit 180 typically causes the web material 100 to flow through the ultrasonic welding unit 80 at a constant speed $V_1$. However, it is possible that the feeding unit 180 may be an integral part of a mechanism of the type known in the art, capable of causing the material in the ultrasonic welding unit 80 to flow with a variable speed $V_1$.

The ultrasonic welding unit 80 typically comprises at least one ultrasonic generator 900, an anvil unit 850 and a sliding table 190.

In the embodiment illustrated in FIGS. 4, 5, 6 and 7, the ultrasonic welding unit 80 comprises two ultrasonic generators 900.

The ultrasonic generators 900 and the anvil unit 850 can be positioned indifferently either above or below the sliding table 190.

In the illustrated embodiment, the ultrasonic generators 900 are positioned below with respect to the sliding table 190 and, consequently, the anvil unit 850 is positioned above said table.

Figure 6:
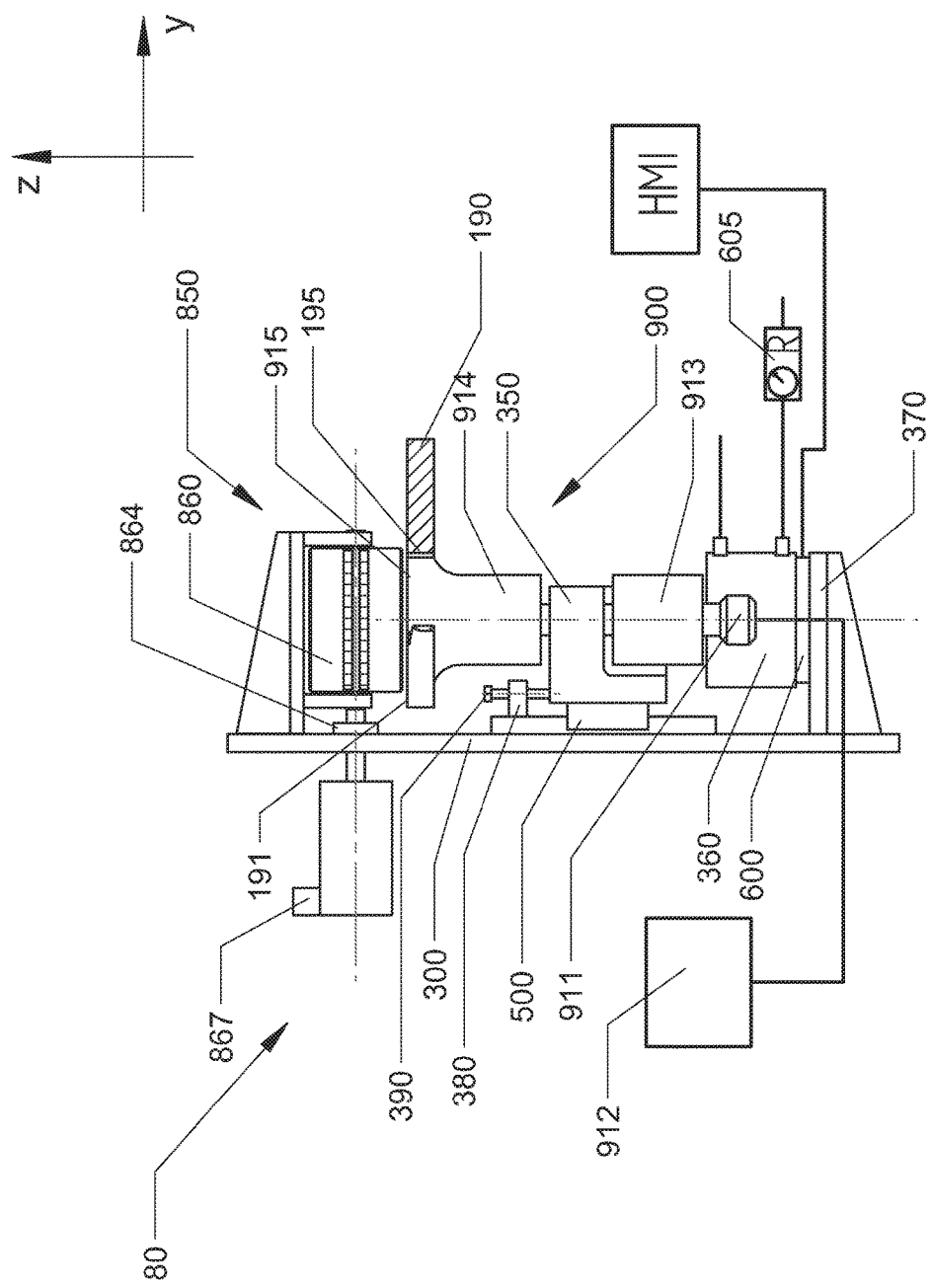
FIG. 6 is a schematic view according to the arrow A of the welding unit of FIG. 5.
Figure 7:
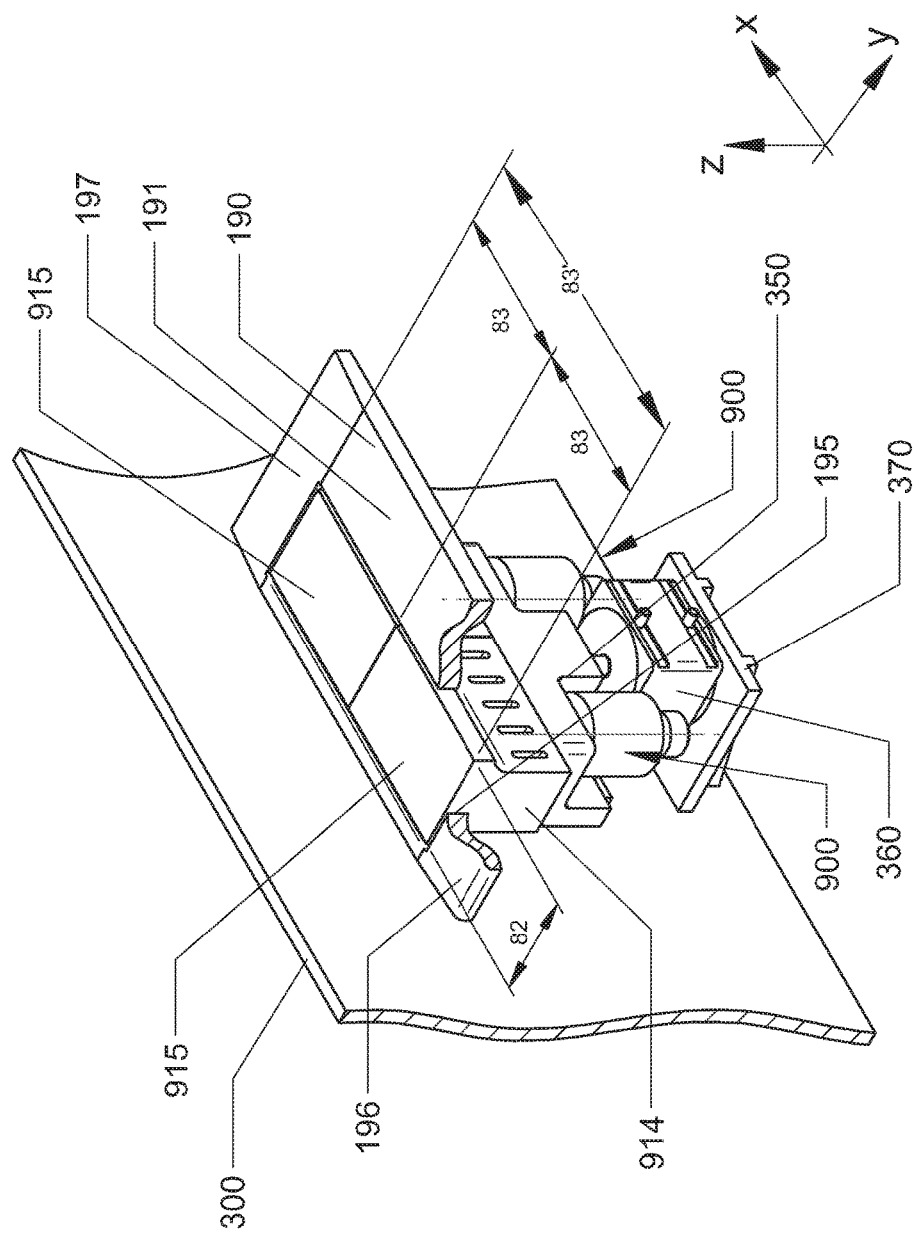
FIG. 7 is a schematic perspective view of the welding unit of FIG. 5 wherein the anvil unit has been removed.

As illustrated in FIG. 6, in each ultrasonic generator 900, it is possible to identify an electrical pulse generator 912, a piezoelectric transducer 911 capable of transforming the electrical impulses into mechanical vibrational energy, by converting them into mechanical movements which, in turn, are amplified by the booster 913 and then sent to the sonotrode 914 which, through its flat welding surface 915, transmits them to the web material 100 that slides on it. In this way, the sonotrode 914 cooperating with the anvil device 850 can form the welding lines 13.

In the ultrasonic generators 900, the outer surfaces 915 of each sonotrode 914 are typically parallel to the movement plane β (beta) of the web material 100.

The flat welding surface 915 of each sonotrode 914 is, in turn, characterized by its dimensions of width 82 and length 83.

The width 82 of the flat welding surface 915, transverse to the main direction X, must be wide enough to support the portion of the web material 100 that is to be subjected to ultrasonic treatment, or rather, in other words, the flat welding surface 915 must typically have an extension 82 in the transverse direction Y equal to or greater than the length L of the transversal welds 13.

The length 83 of the flat welding surface 915, parallel to the main direction X, must be such as to ensure a sufficiently long contact (or crossing or welding) time t between the web 100 that slides at the speed $V_1$ and the ultrasonic welding unit 80 components in order to implement the aforesaid ultrasonic treatment.

Typically, it is possible to obtain an ultrasonic welding unit 80 that has the flat welding surface with the appropriate dimensions of width 82 and length 83 by coupling together two or more ultrasonic generators 900 with the respective flat welding surfaces 915 that are contiguous and coplanar.

In the embodiment illustrated in FIG. 4, an ultrasonic welding unit 80 of suitable dimensions was obtained, by combining two ultrasonic generators 900, one behind the other.

Each sonotrode 914 in fact has a flat welding surface 915 that has a width 82 equal to or greater than the length L of the transverse welds 13, but a length 83 insufficient to be able to guarantee the contact time t necessary to create the welds 13, as will become evident below.

Alternatively, arranging an ultrasonic generator 900 of adequate power and a sonotrode 914, which has the flat welding surface 915 of appropriate dimensions, the ultrasonic welding unit 80 could comprise a single ultrasonic generator 900.

In the illustrated embodiment, the ultrasonic generators 900 of the ultrasonic welding unit 80 are typically mounted on a slide 500.

[moo] Specifically, it is possible to place the transducer 911, the booster 913 and the sonotrode 914 of each ultrasonic generator 900 on a support bracket 350 of suitable rigidity which, in turn, is bound to the frame 300 of the production line through a slide 500 which allows it to only move vertically, parallelly to the Z direction, or rather, at right angles to the flat welding surface 915.

An ultrasonic generator 900 suitable for the applications described here can be provided by Herrmann Ultraschalltechnik GmbH & Co. KG.—Descostrasse 3-9, 76307 Karlsbad—Germany and comprises an Ultrasonic Generator model DYNAMIC digital control 4000 CS, a titanium converter model CCS 20-S-IP50-L-I, a titanium Booster 20 KHz ratio 1:1.4, and a titanium sonotrode 20 KHz ∟=½, MS 85/45/16 Square.

The slide 500 is typically any slide available on the market or which can be made.

An example of a slide 500 suitable for our application can be a dovetail slide, which can be easily designed and created using the disclosures available in the technical literature or produced using components for linear motion, such as linear guides of the HG series produced and marketed by HIWIN Srl—via De Gasperi, 85-20017 Rho (Milan)—Italy.

In the ultrasonic welding unit 80, the vertical movement of the ultrasonic generators 900 can be implemented with any device 360 capable of ensuring a controlled thrust force F.

Figure 5:
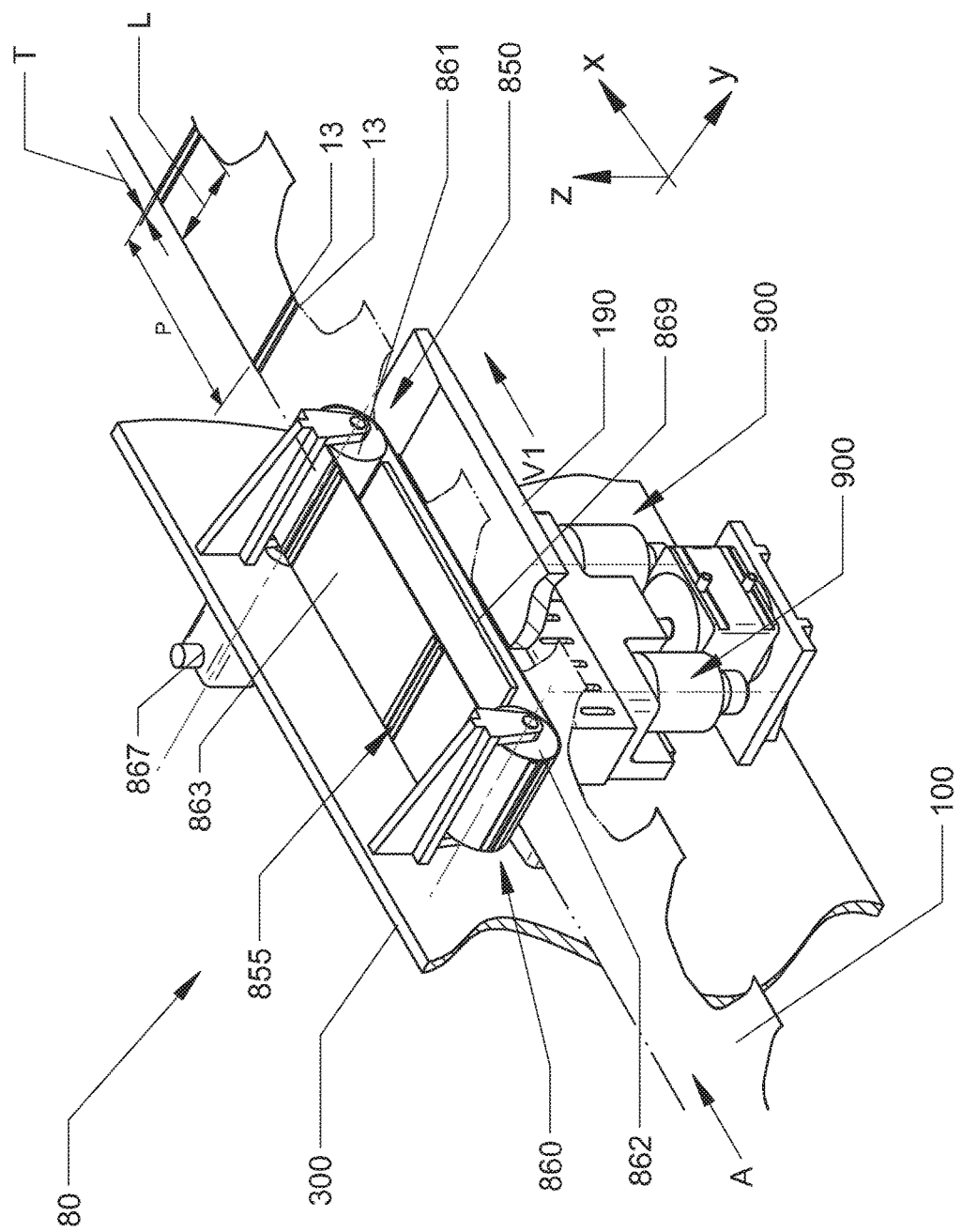
FIG. 5 is a schematic perspective view of the welding unit according to an embodiment of the present invention.
Figure 5B:
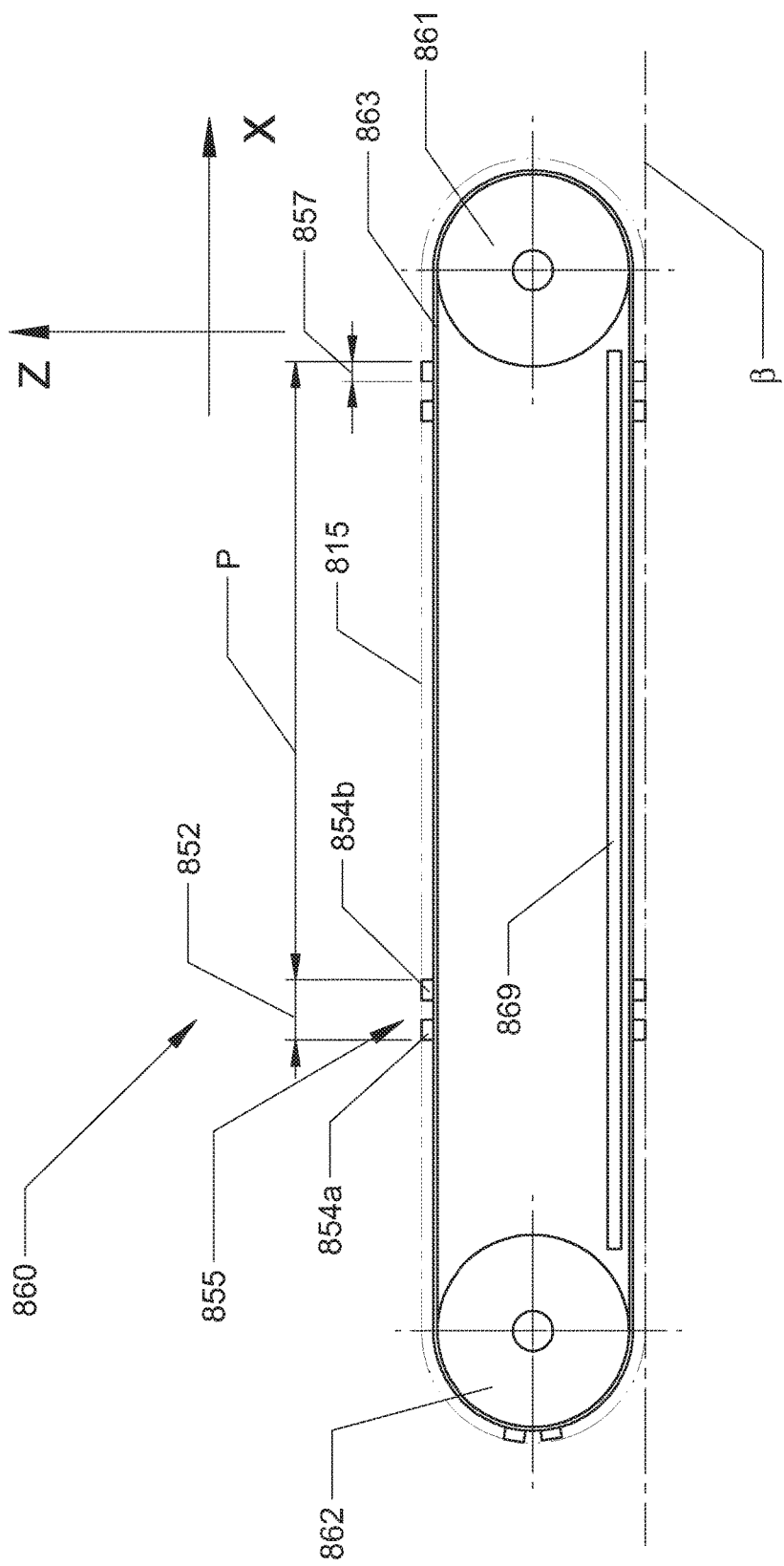
FIG. 5b is a schematic side view of the anvil unit of the welding unit according to an embodiment of the present invention.

Devices with these characteristics are well known in the art and can be produced by means of electric actuators or pneumatic actuators In the embodiment illustrated in FIGS. 5 and 6, the movement of the vibrating units 900 is carried out with a pneumatic actuator 360, which has its upper end connected to the support bracket 350 and the lower end secured to a bracket 370, of suitable shape and dimensions which, in turn, can be fixed to the frame 300 of the production line.

As shown in FIGS. 5 and 6, between the lower end of the pneumatic actuator 360 and the bracket 370, a force detection sensor 600 can be inserted, the function of which will be explained below.

In the illustrated configuration, the pneumatic actuator 360 typically pushes the support bracket 350 upwards and, consequently, the ultrasonic generators 900 bound to it.

In the illustrated embodiment, the stroke of the pneumatic actuator 360 can be limited by a stop element 380, which is also bound to the frame 300, which is typically provided with a precision (micrometer) stroke end recording device 390, which identifies the position that must be occupied by the flat welding surfaces 915 during the welding step.

In the ultrasonic welding unit 80, the flat welding surfaces 915 of the sonotrodes 914 of the ultrasonic generators 900, to be able to produce the welding lines 13, must cooperate with an anvil unit 850 which, in the embodiment illustrated in FIG. 5, can typically comprise a motorized belt transport system 860 of a known type on which a plurality of anvil elements 855 are mounted, typically equidistant from each other.

The belt transport system 860 of the anvil unit 850 can be produced with two pulleys 861 and 862 of suitable width and with a preferably toothed belt 863 that slides between the two.

The belt transport system 860 can be motorized by connecting one of the two pulleys with a mechanical joint 864, typically the pulley 861, to an electric motor 867 which, in the configuration illustrated, may be formed of an electronically-controlled servomotor.

As illustrated in FIG. 5, each anvil element 855 of the anvil unit 850 typically contributes to forming the two welding lines 13 of two consecutive absorbent sanitary articles 10. Therefore, the distance between two consecutive anvil elements 855 is typically equal to the pitch P of production of the machine.

As illustrated in greater detail in FIG. 8, each of the anvil elements 855 typically has a length 853 and a width 852 that are transverse and parallel, respectively, to the main direction X, and comprises a first welding bar 854a and a second welding bar 854b identical to each other and each responsible for producing one of the two welding lines 13 of two consecutive absorbent articles 10.

The two welding bars 854a and 854b, as shown in FIG. 8, may typically be parallel with respect to a Y1-Y1 line perpendicular to the first main direction X and each has a length 853 greater than or equal to the length L of the transverse welds 13 and a width 857, which corresponds to the width T of the welds 13.

In this embodiment the two welding bars 854a and 854b can be independent elements, directly linked to the belt 863 of the motorized conveyor belt 860 by means, for example, of suitable screws 868.

The anvil element 855 and, in particular, the two welding bars 854a and 854b are responsible for the imprint of the welds 13, or rather the conformation assumed by the areas where the absorbent articles are welded due to the effect of ultrasonic treatment. The grooves (or patterns) 851 contribute to define the imprint of the welds 13, and are made on the outer surface 859 of the welding bars 854a and 854b.

In the embodiment illustrated in FIGS. 8 and 9, the patterns 851 are both straight, since the welding lines 13 that are to be produced are straight, and present a toothed motif visible in detail in FIG. 9. In a typical embodiment, each tooth can have the following dimensions: width 858 equal to 0.4 mm, length 857 (corresponding to the width of the pattern 851 and to the width T of the welds 13) 7 mm and a height 849 or depth of 1 mm of the tooth, with a pitch Pp of 1.5 mm between two consecutive teeth.

The choice of a straight trend for the pattern 851 is not of course imperative: this trend is, in fact, dictated by the trend of the welding lines 13 that are to be produced and which may not necessarily be straight. Moreover, the welding patterns 851 may be parallel to each other and perpendicular to the main direction X, but may also not be, forming an overall V-shaped trend with an opening angle at the vertex of the V typically between 5 and 10°, preferably between 6 and 8°.

The outer surface of the welding bars 854a and 854b cooperating with the vibrating plane 915 may have any groove design, in fact, in addition to the toothed motif typically adopted, motifs can be created with different geometric shapes or with fancy shapes such as, for example: triangles, squares, circles, hearts, stars, teddy bears etc. or a combination of these.

In the ultrasonic welding unit 80, the anvil unit 850 is structured so that the anvil elements 855 move along a closed path 815 provided with a straight portion parallel to the main direction X and to the flat vibrating surface 915, and wherein the anvil elements 855 typically have the same speed V1 of the web material 100.

In addition, the anvil unit 850 is structured in such a way that the anvil elements 855 in the closed path section 815 parallel to the main direction X and to the flat vibrating surface 915 retain their outer surface 859 parallel to the aforesaid flat vibrating surface 915 while maintaining their fixed position in the orthogonal directions to the main direction X.

In the embodiment illustrated in FIG. 5, the sliding table 190 on which the web material 100 flows can be provided with a slot 195 in which the ultrasonic generators 900 of the ultrasonic welding unit 80 are inserted, so as to have the flat vibrating surface 915 of each sonotrode 914 coplanar with the upper surface 191 of the table 190, which therefore also results as being parallel to the movement plane L (beta) of the web material 100.

The sliding table 190 typically presents an inlet transition region 196, and an outlet transition region 197, which allow the anvil elements 855 to place themselves parallel to the flat vibrating surface 915 without risking interference, for example, with the absorbent structures 2 present on the web material 100, which have a considerable thickness.

The inlet and outlet transition regions 196 and 197 can be produced by rounding off the sliding table 190 with an angle of 1-5° at the inlet edge and the outlet edge of the flat vibrating surface 915.

In the illustrated embodiment, as mentioned above, the flat vibrating surface 915 of each ultrasound source 900 is typically held in position by the thrust force F of the pneumatic actuator 360, which carries the supporting slide 500 of the vibrating unit 800 to stop against the stroke end recording device 390 of the stop element 380.

Typically, the precision stroke end recording device 390 of the stop element 380 is calibrated without the web material 100 in such a way as to bring the flat vibrating surface 915 so it touches the outer surface 859 of the welding bars 854a and 854b parallel to it.

This particular recording is preferred because it avoids that the flat vibrating surface 915 comes into direct contact with the anvil elements 855 during the various working steps, for example, in the case of accidental breakage of the web material 100.

Therefore, this recording is able to prevent premature wear of the flat vibrating surface 915 of the sonotrodes 914 but, at the same time, allows the web material 100 to be pressed with a predetermined thrust force F between the outer surface 859 of the welding bars 854a and 854b of each anvil element 855 and the flat vibrating surface 915.

During the welding step, the web material 100 at the outlet of the first feeding means 181 slides on the sliding table 190 through the inlet region 196 and is fed to the ultrasonic welding unit 80, in which the anvil element 855 of the anvil unit 850, which typically has a transverse width 853 greater than the length L of the transverse welds 13, presses it with the predetermined thrust force F against the flat welding surface 915, also provided with a width 82 typically greater than or equal to the length L of the welds 13.

During the welding step, the flat welding surface 915 of the ultrasonic welding unit 80 is fixed with respect to the main direction X and the transverse direction Y, while the anvil elements 855 and the web material 100 both slide on the flat welding surface 915, parallel to the plane L L along the main straight direction X at a speed V1.

For all the time t that the web material 100 is engaged in crossing the flat welding surface 915, the latter, in cooperation with the anvil elements 855, transfers the ultrasonic energy required to produce the welds 13 to the web material 100 itself; also in virtue of the fact that during the welding step, the anvil elements 855 have a very high rigidity in the directions (Y, Z) perpendicular to the main direction X.

In the embodiment illustrated in FIG. 5, the means necessary to ensure the aforesaid rigidity of the anvil elements 855 can be a plate 869 suitably fixed to the conveyor 860, which is made to slide on the inner surface of the belt 863 in combination with the pulleys 861 and 862 provided with appropriate lateral guide flanges.

Figure 10:
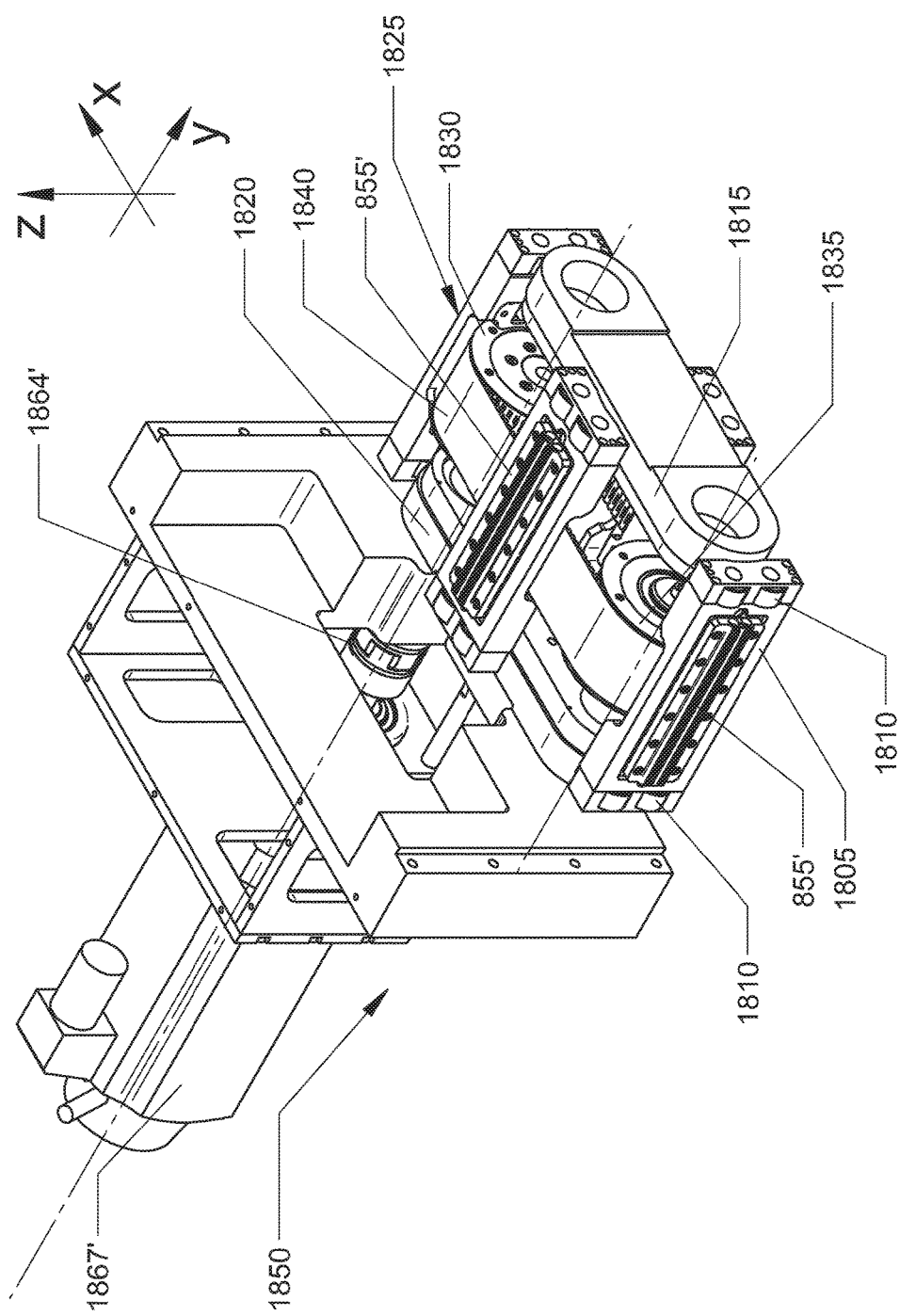
FIG. 10 is a schematic perspective view of an anvil unit according to another embodiment of the present invention.

An anvil unit 1850 according to a further embodiment, which presents extremely rigid anvil elements 855' in the Y and Z directions, is represented in FIGS. 10 and 11.

In the additional embodiment illustrated in FIG. 10, the anvil unit 1850 typically has a plurality of anvil elements 855' provided with a base element 856 from which the two welding bars 854a and 854b protrude, as shown in FIG. 12. In this additional embodiment, it is also possible to have the previously described V-shaped configuration of the welding bars 854a and 854b.

Each of the anvil elements 855' is fixed on a respective transport element (or carriage) 1805.

Each transport element (or carriage) 1805 slides on two guides or rails: one front guide or rail 1815, typically faces towards the line operator, and one rear guide or rail 1820, faces towards the frame of the production machine.

The sliding of each transport element or carriage 1805 on the guides or rails 1815 and 1820 is made easier by the use of appropriate sliding means which, in the embodiment illustrated in FIGS. 10 and 11, can be wheels 1810, which are coupled to the guides or rails 1815 and 1820, preventing the individual carriages 1805 from moving outside the closed path 815 determined by the guides or rails 1815 and 1820 themselves. Therefore, during the welding step, or rather in the lower straight section of the guides 1815 and 1820 parallel to the main direction X, each anvil element 855' is typically pressed against the flat welding surface 915 with the interposition of the web material 100 with a predetermined thrust force F and the sliding means or wheels 1810 are capable of inhibiting any possible unwanted movements while keeping the position of the anvil elements 855' fixed in the directions Y and Z.

In the embodiment illustrated in FIG. 10, the individual carriages 1805 are connected to each other by means of a toothed belt transmission system 1825 of a known type.

The transmission system typically comprises a toothed belt 1840 and a pair of pulleys 1830 and 1835, of which the first pulley 1830, is typically driving, or rather, it is connected by means of a constant velocity joint 1864' to the electric motor 1867', which typically, in this case as well, can be an electronically controlled servomotor, while the second pulley 1835 is the conduct or return pulley.

The criteria for selecting and dimensioning of the toothed belt transmission system 1825 are typically related to factors known to a technical expert such as, for example, the power that the system must transmit and the working speed.

In one embodiment, a toothed belt transmission system with the HTD-type toothed profile can be selected.

To manage the quality of the welds 13 that are made with the welding apparatus 70 according to the present invention, it is possible to intervene on different parameters. In fact, it is possible to intervene not only on the intrinsic parameters of the vibrating units 900, such as the power and the vibration frequency, but also on the thrust force F of the pneumatic actuator 360 and, especially, on the welding time t.

Typically, as illustrated in FIG. 6, the thrust force (or welding force) F can be directly monitored by means of the insertion of a force detection sensor 600 between the bottom of the pneumatic actuator 360 and the bracket 370.

Therefore, once the optimal welding force F has been determined, it can be monitored during its operation with the force detection sensor 600, which typically communicates with an operator interface device or HMI (Human Machine Interface).

For example, the pneumatic actuator 360 may typically be connected to the compressed air distribution network through a pressure regulating device 605, which is able to keep the value of the air pressure in the actuator 360 constant.

A force detection sensor 600 suitable for application in the device shown in the preferred embodiment can be a load cell of the type U10M 1.25 kN-5 kN produced and marketed by HBM Italia Srl—Via Pordenone, 8-20132 Milan, Italy.

To improve the mechanical characteristics of the welds 13, it is also possible to act on the permanence time t of the web material 100 within the welding mechanism 80.

The choice of the welding time t can typically be made in the design step of the welding apparatus 70 taking into due consideration a number of factors including: the number of layers of material which must be joined to each other by means of welding, the type of materials, their chemical composition and the production speed of the machine in meters per second, which is the speed with which the web material 100 flows into the ultrasonic welding unit 80.

Once the above parameters are known, it is possible to determine, also by means of tests, a suitable welding time t.

From tests carried out by the applicant, it has been seen that on lines which have a production speed V1 of 5 m/s, employing the materials commonly used for the construction of the composite web material 100 such as, for example, two layers of non-woven material based on spun bonded 16 g/m2 polypropylene, welds of excellent quality were obtained with welding times t from 0.02 to 0.2 seconds, more preferably between 0.08 and 0.12 seconds. These welding times imply that must be provided an ultrasonic welding unit having a flat welding surface 915 with a total length 83 or 83' between 0.1 and 1.0 meters, more preferably between 0.4 and 0.6 meters.

From the above it follows that to increase the welding time t (or permanence time of the web material 100 within the ultrasonic welding unit 80), it is typically necessary to lengthen both the flat welding surface 915 and the anvil unit 850.

As mentioned above, it is possible to obtain an ultrasonic welding unit 80 provided with a flat welding surface 915 with the appropriate width 82 and especially length 83 or 83' dimensions using two or more ultrasonic generators 900 with the respective flat welding surfaces 915 that are contiguous and coplanar, as shown in FIG. 4 where the flat welding surface 915 of length 83' has been made by combining the sonotrodes 914, one behind the other, of two respective ultrasonic generators 900.

To lengthen the anvil unit 850, it is necessary to insert additional anvil elements 855 consequently elongating the transport system 860, 1825, to equal the specific production pitch P of the machine and the welding.

From what has been said, it is apparent that the elongation of the ultrasonic welding unit 80 can only be carried out in discrete quantities, both regarding the flat welding surface 915, and regarding the anvil unit 850.

In fact, the minimum elongation of the flat welding surface is equal to the length 83 of the single flat welding surface 915 of the ultrasound source 900; while, in the embodiment of FIG. 5 and of FIG. 10, the minimum elongation of the anvil unit 850 is equal to 0.5 P.

During the welding tests carried out by the applicant, it was possible to verify that the web material 100 pressed between the flat welding surface 915 and the anvil elements 855, is only able to slide through the ultrasonic welding unit 80 when the ultrasound sources 900 are functioning. In fact, when the latter are turned off, and therefore their flat welding surface 915 acts as a simple sliding surface, the web material 100 due to the fact that it is pressed against it, presents great difficulties in sliding above it, in some cases resulting in breakage, despite the towing action performed as well as that from the second feeding means 182 and from the anvil unit 850, 1850.

As already said, the web material 100, after being ultrasound-treated is extracted from the ultrasonic welding unit 80 by the second feeding means 182, which enables its subsequent feeding to the cutting station 90, as shown in FIG. 4.

The cutting station 90 can typically comprise a support structure (not shown) on which the cutting roller 92 (or knife) and the contrast roller 93 (or counter-knife or anvil roller) are mounted. The knife roller 92 and anvil roller 93 can be motorized by a motor means 95, which in the illustrated configuration can be formed by an electronically controlled servomotor which, in turn, can be mechanically connected to the knife roller 92 by a suitable constant-velocity joint.

Typically, the knife roller 92 is able to motorize the anvil roller 93 by means of a motion transmission system, which can be of the type with gears that can be splined on the knife roller 92 and on the anvil roller 93, respectively.

The roller knife 92 typically carries at least one cutting blade 94 on its surface, configured to cooperate with the anvil roller 93. In this way, the web material 100, or rather, the completed continuous chain of blanks of articles 10, is segmented into the plurality of disposable sanitary articles 10 by the cutting unit 90 with a plurality of cuts 12, each of which is typically made between the two welding lines 13 of two consecutive sanitary articles 10.

Of course, without prejudice to the principle of the invention, the details of construction and the embodiments may vary, even significantly, with respect to those illustrated here, purely by way of non-limiting example, without departing from the scope of the invention as defined by the attached claims.

The invention claimed is:

1. An apparatus for ultrasonic transverse welding of a composite web comprising at least two superimposed sheet materials, the apparatus comprising:
    a feeding unit including first and second feeding devices configured to advance said composite web along a main direction at a speed; and
    an ultrasonic welding unit arranged between said first and second feeding devices and comprising:
        at least one ultrasonic generator coupled to a sonotrode having a flat welding surface parallel to the plane of movement of the web and fixed in said main direction; and
        an anvil unit having at least one anvil element movable along a closed path having a straight portion parallel to said main direction, said at least one anvil element moving at said speed along said straight portion of said closed path, wherein:
        during use, said at least one anvil element is pressed against said flat welding surface with a predetermined force and with of said composite web material interposed therebetween,
        said at least one anvil element and said flat welding surface have an extension in a transverse direction to said main direction that is equal to or greater than a length of said transverse weld, and
        said flat welding surface has a total length parallel to said main direction between 0.1 and 1.0 meters.

2. An apparatus according to claim 1, wherein said ultrasonic welding unit comprises a plurality of said ultrasonic generators having respective flat welding surfaces that are contiguous and coplanar with each other.

3. An apparatus according to claim 1, wherein said at least one anvil element of said anvil unit is fixed onto a conveyor belt defining said closed path of said at least one anvil element.

4. An apparatus according to claim 1, wherein said at least one anvil element of said anvil unit is fixed on a transport element that can slide on at least one guide defining said closed path of said at least one anvil element.

5. An apparatus according to claim 1, wherein said at least one anvil element comprises two welding bars.

6. An apparatus according to claim 5, wherein said at least one anvil element of said anvil unit is provided with a base element from which said two welding bars protrude.

7. An apparatus according to claim 5, wherein said two welding bars of said at least one anvil element of said anvil unit are parallel to each other and perpendicular to said main direction.

8. An apparatus according to claim 6, wherein said two welding bars of said at least one anvil element have a V-shaped configuration with an opening angle at the vertex of the V between 5 and 10°.

9. An apparatus according to claim 1, wherein said anvil unit at least in said straight portion parallel to said main direction of said closed path comprises devices configured to maintain a fixed position of said at least one anvil element in said directions orthogonal to said main direction.

10. An apparatus according to claim 1, wherein said length parallel to said main direction of said flat welding surface of said at least one ultrasonic generator is greater than or equal to a width of said at least one anvil element parallel to said main direction.

11. An apparatus according to claim 1, wherein said flat welding surface and said anvil unit define, during operation, a welding time between 0.02 and 0.2 seconds.

12. An apparatus according to claim 1, wherein said anvil unit comprises a plurality of said anvil elements that are equidistant from each other.

* * * * *